(12) United States Patent
Elidrissi et al.

(10) Patent No.: US 11,742,680 B2
(45) Date of Patent: Aug. 29, 2023

(54) DYNAMIC MANAGEMENT OF CHARGE

(71) Applicant: Medtronic MiniMed, Inc., Northridge, CA (US)

(72) Inventors: Jalal Elidrissi, Santa Clarita, CA (US); Adam S. Trock, Simi Valley, CA (US); Fatemeh Delijani, Chatworth, CA (US); Seth N. Kazarians, Duarte, CA (US); Zhaleh Lotfi, Northridge, CA (US); Afshin Bazargan, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 172 days.

(21) Appl. No.: 16/997,232

(22) Filed: Aug. 19, 2020

(65) Prior Publication Data

US 2021/0281093 A1 Sep. 9, 2021

Related U.S. Application Data

(60) Provisional application No. 62/987,122, filed on Mar. 9, 2020.

(51) Int. Cl.
*H02J 7/00* (2006.01)
*A61M 5/142* (2006.01)

(52) U.S. Cl.
CPC ........... *H02J 7/0049* (2020.01); *A61M 5/142* (2013.01); *H02J 7/007* (2013.01); *H02J 7/00032* (2020.01);
(Continued)

(58) Field of Classification Search
CPC combination set(s) only.
See application file for complete search history.

(56) References Cited

U.S. PATENT DOCUMENTS 4,562,751 A 1/1986 Nason et al.
4,685,903 A 8/1987 Cable et al.
(Continued)

FOREIGN PATENT DOCUMENTS

DE 102017209489 A1 * 12/2018 .......... B60L 11/1809
DE 102017209489 A1 12/2018
(Continued)

OTHER PUBLICATIONS

DE-102017209489-A1,Diekmann R Diekmann R translation.*
(Continued)

*Primary Examiner* — Drew A Dunn
*Assistant Examiner* — Tynese V McDaniel
(74) *Attorney, Agent, or Firm* — Weaver Austin Villeneuve & Sampson LLP

(57) ABSTRACT

Embodiments are provided for dynamic management of charge. A method involves obtaining an estimated readiness time for an energy storage element, obtaining a target state of charge for the energy storage element, calculating an estimated charging time based at least in part on a difference between the target state of charge and a current state of charge, using a first charging rate to charge the energy storage element to an intermediate state of charge responsive to determining a time difference between the estimated readiness time and a first time is greater than the estimated charging time, maintaining the energy storage element at the intermediate state of charge, and responsive to determining a time difference between the estimated readiness time and a second time is less than the estimated charging time, using a second charging rate to charge the energy storage element to the target state of charge.

20 Claims, 5 Drawing Sheets

(52) U.S. Cl.
CPC ........ *H02J 7/00034* (2020.01); *H02J 7/0048* (2020.01); *A61M 5/14244* (2013.01); *A61M 2205/18* (2013.01); *A61M 2205/3584* (2013.01); *A61M 2205/52* (2013.01); *A61M 2205/8206* (2013.01)

(56) References Cited

U.S. PATENT DOCUMENTS

| | | | |
|---|---|---|---|
| 5,080,653 | A | 1/1992 | Voss et al. |
| 5,097,122 | A | 3/1992 | Colman et al. |
| 5,505,709 | A | 4/1996 | Funderburk et al. |
| 6,485,465 | B2 | 11/2002 | Moberg et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,641,533 | B2 | 11/2003 | Causey, III et al. |
| 6,659,980 | B2 | 12/2003 | Moberg et al. |
| 6,752,787 | B1 | 6/2004 | Causey, III et al. |
| 6,817,990 | B2 | 11/2004 | Yap et al. |
| 6,932,584 | B2 | 8/2005 | Gray et al. |
| 7,621,893 | B2 | 11/2009 | Moberg et al. |
| 7,704,227 | B2 | 4/2010 | Moberg et al. |
| 9,867,017 | B1 | 1/2018 | Bacarella et al. |
| 9,955,313 | B1 | 4/2018 | Bacarella et al. |
| 2004/0193025 | A1 | 9/2004 | Steil et al. |
| 2009/0021218 | A1 | 1/2009 | Kelty et al. |
| 2010/0160861 | A1 | 6/2010 | Causey, III et al. |
| 2010/0324382 | A1 | 12/2010 | Cantwell et al. |
| 2011/0018679 | A1 | 1/2011 | Davis et al. |
| 2011/0314319 | A1 | 12/2011 | Kurahashi |
| 2014/0236379 | A1* | 8/2014 | Masuda ................ H01M 10/44 700/297 |
| 2014/0253037 | A1 | 9/2014 | Yano et al. |
| 2015/0188324 | A1* | 7/2015 | Nicholson ............ H02J 7/0088 320/128 |
| 2015/0369871 | A1* | 12/2015 | Nishigaki ........... H01M 10/425 324/426 |
| 2016/0064960 | A1* | 3/2016 | DiCarlo .................... H02J 7/00 320/134 |
| 2018/0115170 | A1 | 4/2018 | Bacarella et al. |
| 2018/0115871 | A1 | 4/2018 | Bacarella et al. |
| 2018/0115955 | A1 | 4/2018 | Bacarella et al. |
| 2019/0207397 | A1 | 7/2019 | Lai et al. |
| 2019/0229547 | A1* | 7/2019 | Lim .................... H01M 10/425 |
| 2019/0334353 | A1 | 10/2019 | Solomon |
| 2020/0307405 | A1* | 10/2020 | Waardenburg ........ B60L 53/665 |
| 2021/0152004 | A1* | 5/2021 | Basehore ............. H02J 7/0069 |
| 2021/0281093 | A1 | 9/2021 | Elidrissi et al. |
| 2021/0288509 | A1 | 9/2021 | Werner et al. |
| 2021/0396816 | A1 | 12/2021 | Zominy et al. |
| 2022/0077691 | A1* | 3/2022 | Jeong ................. H02J 7/00714 |

FOREIGN PATENT DOCUMENTS

| | | |
|---|---|---|
| WO | 0152727 A1 | 7/2001 |
| WO | 2016196467 A1 | 12/2016 |

OTHER PUBLICATIONS

International Search Report and Written Opinion of International Application No. PCT/US2021/020194, dated Jul. 1, 2021, 14 pp.

U.S. Appl. No. 16/997,260, Naming Inventors: Elidrissi et al., filed Aug. 19, 2020.

\* cited by examiner

DYNAMIC MANAGEMENT OF CHARGE

CROSS-REFERENCE TO RELATED APPLICATION(S)

This application claims the benefit of U.S. Provisional Patent Application Ser. No. 62/987,122, filed Mar. 9, 2020, the contents of which are incorporated by reference herein in its entirety.

TECHNICAL FIELD

Embodiments of the subject matter described herein relate generally to energy storage technology, and more particularly, embodiments of the subject matter relate to dynamic management of charge.

BACKGROUND

Advances in battery technology have facilitated the popularity of battery-powered devices (e.g., medical devices, electric cars, laptop computers, and smartphones) in modern society. Examples of battery-powered devices include portable or wearable infusion pump devices and systems for use in delivering or dispensing an agent, such as insulin and/or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Many batteries are rechargeable. However, rechargeable batteries are often maintained in a manner that results in shortened battery life. For example, accelerated degradation may result from maintaining batteries at a low state of charge for a prolonged period of time, maintaining batteries at a maximum state of charge for a prolonged period of time, recharging batteries too frequently, and charging batteries too quickly. Accordingly, techniques for mitigating accelerated degradation are desirable. Other desirable features and characteristics will become apparent from the subsequent detailed description and the appended claims, taken in conjunction with the accompanying drawings and this background.

BRIEF SUMMARY

Disclosed herein are embodiments related to dynamic management of charge. In some embodiments, a processor-implemented method involves obtaining an estimated readiness time for an energy storage element, obtaining a target state of charge for the energy storage element, calculating an estimated charging time based at least in part on a difference between the target state of charge and a current state of charge of the energy storage element, using a first charging rate to charge the energy storage element to an intermediate state of charge responsive to determining a time difference between the estimated readiness time and a first point in time is greater than the estimated charging time, maintaining the energy storage element at the intermediate state of charge, and responsive to determining a time difference between the estimated readiness time and a second point in time is less than the estimated charging time, using a second charging rate to charge the energy storage element to the target state of charge. The second point in time is after the first point in time, and the second charging rate is greater than the first charging rate.

In some embodiments, one or more non-transitory processor-readable storage media store instructions that, when executed by one or more processors, cause performance of: obtaining an estimated readiness time for an energy storage element, obtaining a target state of charge for the energy storage element, calculating an estimated charging time based at least in part on a difference between the target state of charge and a current state of charge of the energy storage element, responsive to determining a time difference between the estimated readiness time and a first point in time is greater than the estimated charging time, using a first charging rate to charge the energy storage element to an intermediate state of charge, maintaining the energy storage element at the intermediate state of charge, and responsive to determining a time difference between the estimated readiness time and a second point in time is less than the estimated charging time, using a second charging rate to charge the energy storage element to the target state of charge, wherein the second point in time is after the first point in time, and wherein the second charging rate is greater than the first charging rate.

In some embodiments, a system is provided that includes one or more processors and one or more processor-readable storage media storing instructions which, when executed by the one or more processors, cause performance of: obtaining an estimated readiness time for an energy storage element, obtaining a target state of charge for the energy storage element, calculating an estimated charging time based at least in part on a difference between the target state of charge and a current state of charge of the energy storage element, responsive to determining a time difference between the estimated readiness time and a first point in time is greater than the estimated charging time, using a first charging rate to charge the energy storage element to an intermediate state of charge, maintaining the energy storage element at the intermediate state of charge, and responsive to determining a time difference between the estimated readiness time and a second point in time is less than the estimated charging time, using a second charging rate to charge the energy storage element to the target state of charge, wherein the second point in time is after the first point in time, and wherein the second charging rate is greater than the first charging rate.

In some embodiments, a processor-implemented method involves charging an energy storage element from an initial state of charge to a holding state of charge, maintaining the energy storage element at the holding state of charge, receiving, via a network, an indication to complete charging the energy storage element, and in response to receiving the indication, charging the energy storage element from the holding state of charge to a target state of charge.

In some embodiments, a system is provided that includes one or more processors and one or more processor-readable storage media storing instructions which, when executed by the one or more processors, cause performance of: charging an energy storage element from an initial state of charge to a holding state of charge, maintaining the energy storage element at the holding state of charge, receiving, via a network, an indication to complete charging the energy storage element, and in response to receiving the indication, charging the energy storage element from the holding state of charge to a target state of charge.

In some embodiments, one or more non-transitory processor-readable storage media store instructions that, when executed by one or more processors, cause performance of: charging an energy storage element from an initial state of charge to a holding state of charge, maintaining the energy storage element at the holding state of charge, receiving, via a network, an indication to complete charging the energy storage element, and in response to receiving the indication, charging the energy storage element from the holding state of charge to a target state of charge.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
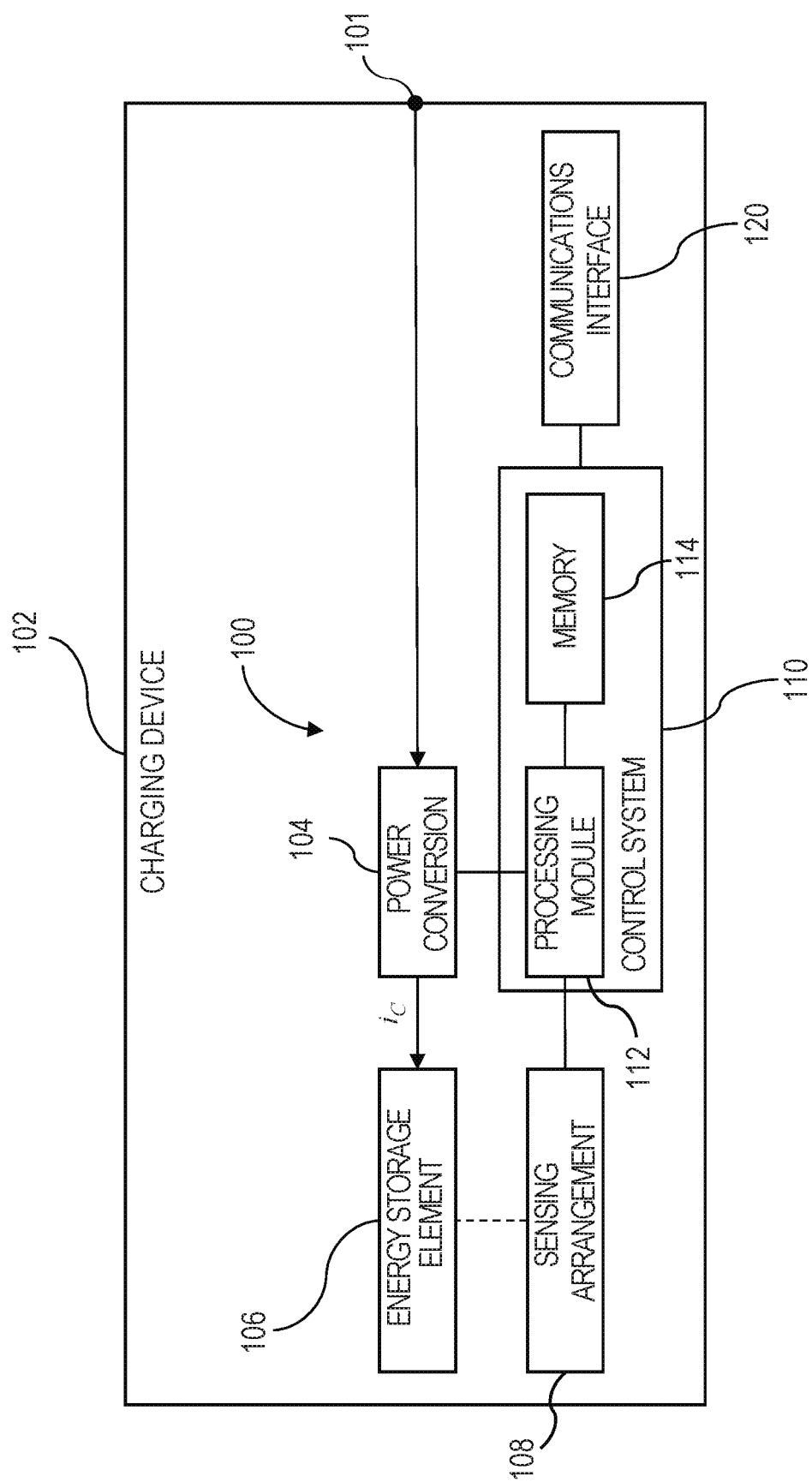
FIG. 1 depicts an exemplary embodiment of a charging system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented with any energy storage element, exemplary embodiments of the subject matter described herein are implemented in conjunction with energy storage elements for use with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of any other device, including other medical devices, such as continuous glucose monitors (CGM) or other sensing devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. For purposes of explanation, the subject matter may be described herein in the context of the infused fluid being insulin for regulating a glucose level of a user (or patient); however, it should be appreciated that many other fluids may be administered through infusion, and the subject matter described herein is not necessarily limited to use with insulin.

Embodiments of the subject matter described herein generally pertain to dynamically managed charging of a rechargeable energy storage element, such as a battery, for use with a battery-powered device based on historical usage data associated with the energy storage element and/or the device. For example, as described in greater detail below in the context of FIGS. 1-3, an estimated readiness time (e.g., a time representing when the energy storage element is predicted to be put into service for powering a device) is identified or otherwise determined based on the duration of one or more preceding charging cycles. To mitigate accelerated battery degradation, charging can be configured to terminate at the estimated readiness time.

As described below, the estimated readiness time may be determined based on a user's historical activity, for example, by averaging the duration(s) of one or more preceding charging cycles (e.g., a time period that begins when the user docks or otherwise connects a battery to a power source and ends when the user disconnects the battery from the power source). If there is a sufficient amount of time remaining until the expected termination of the current charging cycle, the energy storage element may be charged in different charging stages to increase the duration of time that the state of charge of the energy storage element is at or near a holding state of charge (e.g., a 50% state of charge). In this regard, the holding state of charge is intended to mitigate degradation or wear by prolonging the duration of time the energy storage element spends at the holding state of charge and reducing the duration of time the energy storage element spends at a relatively higher and/or final state of charge.

In some embodiments, different charging rates are employed during the different charging stages to enable reaching a targeted final state of charge by the end of the charging cycle. The charging rate that is employed may depend on the current state of charge of the energy storage element. For example, if the current state of charge is less than the holding state of charge, a relatively slow charging rate may be employed to reduce the amount of temperature increase associated with charging.

In some embodiments, the targeted final state of charge is determined based on historical charging data or other historical usage data associated with the energy storage element and/or the device. For example, if historical usage patterns indicate that the energy storage element is not fully discharged in each usage cycle, the targeted final state of charge may be reduced such that the energy storage element is not fully charged at the end of a charging cycle.

As described in greater detail below primarily in the context of FIGS. 4-5, in some embodiments, the estimated readiness time may be dynamically determined in response to one or more communications from one or more devices external to a charging device (e.g., a paired mobile phone or a remote server external to a charging device). The one or more communications may cause adjustment of the estimated readiness time. In this manner, charging behavior may dynamically adapt to changes in user behavior or device usage. For example, a charging device may initially charge an energy storage element to the holding state of charge and maintain the energy storage element at the holding state of charge until the charging device receives an indication from another device to charge the energy storage element to the targeted final state of charge. Thus, when the originally estimated readiness time is changed to an earlier point in time, the charging behavior may dynamically adapt to enable reaching the targeted final state of charge by the earlier point in time. Conversely, when the originally estimated readiness time is changed to a later point in time, the charging behavior may dynamically adapt to delay charging to the targeted final state of charge and thereby increase the duration of time that the energy storage element is maintained at the holding state of charge.

For example, an individual patient may utilize two different infusion devices that each have one or more built-in rechargeable batteries (or the patient may utilize an infusion device with two sets of one or more swappable rechargeable batteries). The infusion device (or battery) that is not currently in use may be charged to the holding state of charge and maintained there while the other infusion device (or battery) is in use. As the state of charge of the in-use infusion device (or battery) becomes depleted, an indication may be transmitted or otherwise provided to the charging infusion device (or battery) to initiate charging from the holding state of charge to the targeted state of charge.

In some embodiments, the patient's mobile device may be paired with his or her infusion devices to enable wireless communications over a wireless personal area network (e.g., a Bluetooth Low Energy (BLE) network) to enable an application or software process at the mobile phone to monitor the state of charge of the in-use infusion device and transmit an indication to the charging infusion device when the state of charge of the in-use infusion device falls below a threshold level. In some other embodiments, the patient's mobile device may transmit or otherwise upload indicia of the state of charge of the in-use infusion device to a remote device over a communications network, and the remote device may provide an indication to the charging infusion device based on the state of charge of the in-use infusion device.

Similarly, in embodiments where an infusion device or other portable medical device utilizes one or more swappable rechargeable batteries, a battery charger or other distinct, standalone charging device may be paired with a patient's mobile device or otherwise configured to support communications with the mobile device (or a remote device communicatively coupled to the battery charger) over a network to facilitate dynamic management of battery charge.

In some embodiments, the subject matter described herein is implemented in the context of an infusion system that includes two infusion devices associated with a patient, where each infusion device includes durable components (e.g., battery and electronics) and consumable components (e.g., a cannula, a reservoir of insulin, etc.). The consumable components may have varying lifespans, and the duration in which the infusion device is in use may be limited by the shortest lifespan of the consumable components. To minimize time without therapy, the infusion device that is being charged is expected to be ready for use when it is time to replace one or more consumable components of the other infusion device.

The techniques described herein may be utilized to dynamically manage battery charge in such a manner that mitigates premature battery degradation while minimizing time without therapy. The techniques described herein may also ensure that the final state of charge of a battery is such that the battery can remain in use throughout the lifespan of any consumables associated with the device powered by the battery.

Dynamic Management of Charge

FIG. 1 depicts an exemplary embodiment of a charging system 100 that may be implemented by an electronic device 102 to charge a rechargeable energy storage element 106. Depending on the embodiment, the electronic device 102 may be realized as a portable medical device (e.g., an infusion device, a CGM device, or the like) or another a portable electronic device (e.g., a mobile phone, a smartphone, a laptop, or other client electronic device) that includes integrated charging capabilities. Alternatively, the electronic device 102 could be realized as a standalone charging device (e.g., a battery charger, a charging dock, a charging station, or the like) that receives a swappable or interchangeable energy storage element 106 that is used to power another portable electronic device. Accordingly, for purposes of explanation, but without limitation, the electronic device 102 may alternatively be referred to herein as a charging device. The illustrated charging system 100 includes, without limitation, a power conversion arrangement 104, a sensing arrangement 108, and a control system 110. It should be appreciated that FIG. 1 depicts a simplified representation of the charging system 100 for purposes of explanation and is not intended to limit the subject matter described herein.

In exemplary embodiments, the energy storage element 106 is realized as one or more rechargeable batteries (or a battery pack), such as, for example, one or more nickel metal hydride batteries, nickel-cadmium batteries, lithium polymer batteries, lithium-ion batteries, lead-acid batteries, or the like. Accordingly, for purposes of explanation, but without limitation, the energy storage element 106 may alternatively be referred to herein as a battery.

The power conversion arrangement 104 generally represents a power converter or other suitable hardware and/or circuitry that is capable of providing electrical energy from an external source to the battery 106 to charge the battery 106. In this regard, the power conversion arrangement 104 generally includes one or more inputs that are coupled to a corresponding input interface 101 that is configured to receive input electrical power. For example, the input interface 101 may be realized as a plug that supports establishing electrical connection to an electrical grid or mains electricity to receive alternating current (AC) electrical signals, where the power conversion arrangement 104 is realized as a rectifier or other AC-to-direct current (DC) converter to provide a DC charging current or voltage at the output of the power conversion arrangement 104. The output of the power conversion arrangement 104 is coupled to a corresponding output interface that facilitates an electrical connection with the battery 106. For example, when the battery 106 is physically separate from the charging device 102, the output of the power conversion arrangement 104 may be electrically connected to a physical interface (e.g., terminals, connectors, and the like) that is configured to mate with a corresponding interface of the battery 106. That said, in other embodiments, when the battery 106 is integrated or contained within the housing of the charging device 102, the output of the power conversion arrangement 104 may be electrically connected to a bus that routes or otherwise provides energy to one or more components of the charging device 102. For example, a positive output node or terminal of the power conversion arrangement 104 may be connected to a supply voltage bus, which, in turn, is connected to a positive terminal of the battery 106, while the negative output node or terminal of the power conversion arrangement 104 is connected to a ground voltage bus, which, in turn, is connected to a negative terminal of the battery 106.

The sensing arrangement 108 generally represents the sensing element(s) of the charging device 102 that are configured to support monitoring one or more of the state of charge of the battery 106, the voltage of the battery 106, and/or the current flow to the battery 106 to track or otherwise monitor the charging status and/or usage of the battery 106. In this regard, the sensing arrangement 108 may include one or more state of charge sensors, voltage sensors, current sensors, coulomb counters, and/or the like. Depending on the embodiment and particular type of sensing technologies being deployed, the sensing arrangement 108 may be connected to the battery interface or battery terminals, or alternatively connected between the power conversion arrangement 104 and the battery 106. It should also be noted that various different types or combinations of sensors or sensing technologies may be utilized, and the subject matter described herein is not limited to any particular type, number, configuration, or combination of sensing elements.

The control system 110 generally represents the component of the charging device 102 that is coupled to the sensing arrangement 108 to monitor the status and usage of the battery 106. As described in greater detail below, the control system 110 operates the power conversion arrangement 104 to dynamically charge the battery 106 in a manner that prolongs the life of the battery 106. In the illustrated embodiment, the control system 110 includes processing module 112 and a data storage element 114. Depending on the embodiment, the processing module 112 may be implemented or realized with a processor, a controller, a microprocessor, a microcontroller, a content addressable memory, a digital signal processor, an application specific integrated circuit, a field programmable gate array, any suitable programmable logic device, discrete gate or transistor logic, processing core, discrete hardware components, or any combination thereof, and configured to carry out the functions, techniques, and processing tasks associated with the operation of the charging system 100 described in greater detail below. Furthermore, the steps of a method or algorithm described in connection with the embodiments disclosed herein may be embodied directly in hardware, in firmware, in a software module executed by the processing module 112, or in any practical combination thereof. In accordance with one or more embodiments, the processing module 112 accesses the data storage element 114, which may be realized as a memory (e.g., RAM memory, ROM memory, flash memory, registers, a hard disk, or the like) or another suitable non-transitory short or long term storage media capable of storing computer-executable programming instructions or other data for execution that, when read and executed by the processing module 112, cause the processing module 112 to execute, facilitate, or perform one or more of the processes, tasks, operations, and/or functions described herein. In exemplary embodiments, the data storage element 114 is also utilized to store or otherwise maintain usage data associated with the battery 106, as described in greater detail below.

Still referring to FIG. 1, in one or more embodiments, the charging device 102 also includes a communications interface 120 that is coupled to the control system 110 and configured to support communications to/from the charging device 102 via a communications network. In this regard, the communications interface 120 generally includes one or more transceivers or communication devices capable of supporting wireless communications between the charging device 102 and another electronic device (e.g., an infusion device, a client device, a remote device, or another electronic device in an infusion system). For example, in one or more exemplary embodiments, the communications interface 120 is realized as a Bluetooth transceiver or adapter configured to support Bluetooth Low Energy (BLE) communications over a Bluetooth network or similar wireless personal area network. In such embodiments, the charging device 102 may establish an association (or pairing) with another external device over the network to support subsequently establishing a point-to-point communications session between the charging device 102 and the external device via the personal area network, for example, by performing a discovery procedure or another suitable pairing procedure to obtain and store network identification information for one another. The pairing information obtained during the discovery procedure allows either of the charging device 102 or the external device to initiate the establishment of a communications session via the personal area network. In yet other embodiments, the communications interface 120 may be configured to support communications with a remote device or other external device over the Internet, a cellular network, a wide area network (WAN), or the like. In this regard, the subject matter described herein is not intended to be limited to any particular type of communications interface 120 or communications network. Moreover, some embodiments described herein may be implemented without inclusion or reliance on a communications interface 120, and in such embodiments, the charging system 100 and/or the charging device 102 may not include a communications interface 120 in practice.

Figure 2:
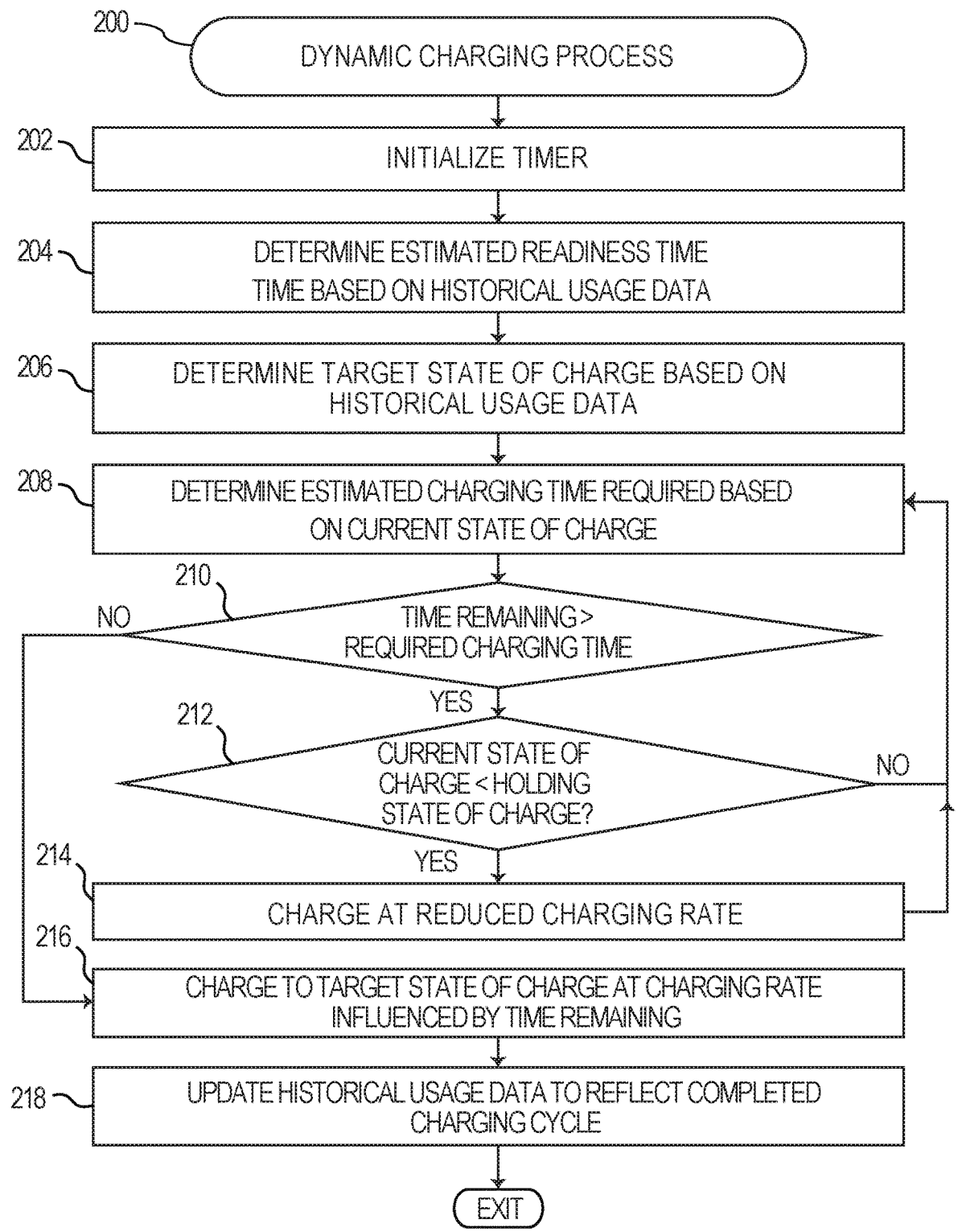
FIG. 2 is a flow diagram of an exemplary charging process suitable for implementation in connection with operation of a charging device in the charging system of FIG. 1 in one or more exemplary embodiments.

FIG. 2 depicts an exemplary embodiment of a dynamic charging process 200 suitable for implementation by the charging system 100 of FIG. 1 to prolong the lifetime of the battery 106. The various tasks performed in connection with the dynamic charging process 200 may be performed by hardware, firmware, software executed by processing circuitry, or any combination thereof. For illustrative purposes, the following description refers to elements mentioned above in connection with FIG. 1. For purposes of explanation, the dynamic charging process 200 may be described herein primarily in the context of being implemented by the control system 110 and/or processing module 112. It should be appreciated that the dynamic charging process 200 may include any number of additional or alternative tasks, the tasks need not be performed in the illustrated order and/or the tasks may be performed concurrently, and/or the dynamic charging process 200 may be incorporated into a more comprehensive procedure or process having additional functionality not described in detail herein. Moreover, one or more of the tasks shown and described in the context of FIG. 2 could be omitted from a practical embodiment of the dynamic charging process 200 as long as the intended overall functionality remains intact.

Referring to FIG. 2, with continued reference to FIG. 1, prior to initiating charging of the energy storage element, the dynamic charging process 200 initializes or otherwise begins by initiating a timer, counter, or similar feature for monitoring a duration of a charging cycle in response to detecting a desire to charge an energy storage element (task 202). For example, in embodiments where the battery 106 is realized as a standalone component, the control system 110 may detect or otherwise identify when the battery 106 is engaged with the charging device 102, for example, by inserting the battery 106 into a port or dock of the charging device 102 or otherwise establishing an electrical connection between the output of the power conversion arrangement 104 and the battery 106. In other embodiments, where the battery 106 is integrated or otherwise housed within the charging device 102, the control system 110 may detect or otherwise identify when the input interface 101 is connected to an external power source (e.g., the mains electricity). In response to detecting a desire to charge the battery 106, the control system 110 and/or processing module 112 resets or otherwise initializes a timer, counter, or similar feature for measuring the duration of the subsequent charging cycle.

As described in greater detail below, the dynamic charging process 200 tracks the duration of each charging cycle between the point in time when the charging device 102 or the battery 106 is initially connected to a source of electrical energy (e.g., the interface 101 of the charging device 102 being connected to an external power supply, the battery 106 being inserted into the charging device 102 and connected to the output of the power conversion arrangement 103, or the like) and when the charging device 102 and/or the battery 106 is subsequently disconnected from charging. The duration between connection and disconnection events is stored or otherwise maintained (e.g., in data storage element 114) as part of the historical usage data associated with the charging device 102 and/or battery 106, which, in turn, is utilized to learn and predict the charging behavior for the charging device 102 and/or battery 106, as described in greater detail below. In one or more embodiments, the timer or counter is also utilized to monitor or track the duration between disconnection or termination of charging and a subsequent connection for recharging the battery 106, to thereby track the duration of time during which the battery 106 is use, that is, the duration of a usage cycle (or discharge cycle) between two otherwise successive charging cycles. Additionally, values of the timer or counter implemented by the control system 110 may be utilized to assign timestamps to measured voltage values, state of charge values, or other data associated with the charging cycle as well as track the duration of the different stages of the charging cycle. For example, as described in greater detail below, the historical data may be utilized to dynamically determine the estimated amount of time required to charge the battery 106 from the initial state of charge to the holding state of charge in an initial charging stage, the estimated amount of time required to charge the battery 106 from the holding state of charge to the targeted final state of charge in a final charging stage, and the like.

Still referring to FIG. 2, the illustrated dynamic charging process 200 calculates or otherwise determines an estimated readiness time for when the current charging cycle is likely to be expected by the user to have been completed based on historical usage data (task 204). In this regard, the estimated readiness time represents the predicted or expected amount of time for which the user is likely to charge the battery 106 during the current charging cycle before resuming use or discharge of the battery 106, that is, the anticipated point in time in the future at which the user is likely to remove the battery 106 from the charging device 102 or disconnect the charging device 102 from an external power supply to terminate charging (e.g., the expected charging cycle termination time). In one or more embodiments, the estimated readiness time is calculated by averaging the durations of preceding charging cycles. For example, the control system 110 and/or processing module 112 may calculate the estimated duration for the current charging cycle as a weighted average of the durations of preceding charging cycles, that is, a weighted average of the durations of time between successive connections to and disconnections from the external power supply. As described in greater detail below, in some embodiments, the standard deviation or some other statistical metric representing the variability in the durations of preceding charging cycles may be utilized to provide a buffer time that advances the estimated readiness time earlier than average or otherwise ensures charging is completed before disconnection would be expected based on the user's historical usage data to increase the probability that the user does not attempt to return the battery to use before the battery is charged to the targeted final state of charge.

In one or more embodiments, where the charging device 102 and/or the battery 106 are utilized in a system where one battery 106 is in use while another battery 106 is charging, the estimated duration for the current charging cycle for a given battery 106 is calculated as a weighted average of the durations of preceding charging cycles for the battery 106 and the durations of the intervening periods during which the battery 106 is in use or discharging (e.g., while the other battery 106 is charging), less some buffer time. For example, the average duration between sequential connection and disconnection events over 10 preceding alternating charging and discharge cycles may be calculated using the equation $$T_S = \sum_{n=0}^{9} (T_{DISC(n+1)} - T_{DISC(n)})/10,$$

where $T_{DISC(n)}$ represents the duration of a respective preceding charging cycle or a respective preceding discharging cycle. Alternatively, the same equation could be utilized to calculate the average duration between sequential connection and disconnection events over preceding alternating charging and discharging cycles where $T_{DISC(n)}$ represents the timestamp values associated with respective connection or disconnection events). It should be appreciated there are numerous different manners in which preceding charging and/or discharging cycle durations may be combined to arrive at an estimated or predicted duration for the current charging cycle (e.g., an estimated readiness time) based on an individual user's historical usage behavior, and the subject matter described herein is not limited to any particular equation or technique.

In some embodiments, the standard deviation associated with the durations of the preceding charging cycles may be utilized to determine a buffer time to be subtracted from the average duration or otherwise utilized to arrive at an estimated duration of time relative to the onset of the charging cycle by when the battery should be ready for return to use that is earlier than the estimated readiness time that would otherwise be arrived at from merely averaging the durations of preceding charging cycles. That said, in other embodiments, the buffer time or wait time ($T_W$) may be incorporated into a calculation or estimation of the amount of time required to charge the battery to achieve the same effect rather than adjusting the estimated readiness time.

The dynamic charging process 200 also calculates or otherwise determines a targeted final state of charge for the charging cycle based on historical usage data (task 206). In exemplary embodiments, the targeted final state of charge is dynamically determined in a manner that is influenced by preceding usage of the battery 106 to reduce the maximum state of charge of the battery 106 to a likely maximum amount of charge required or desired by a user to avoid discharging the battery 106 below a minimum state of charge during the next discharge cycle rather than fully charging the battery 106 (and overcharging relative to its expected usage) to prolong lifetime. The targeted final state of charge may initially be set to a default value of 100% and then be dynamically adjusted and reduced over time to reflect a given individual user's charging or usage behavior based on the respective amounts by which the battery 106 was discharged over preceding usage cycles (e.g., the differences between the final state of charge from a preceding charging cycle and the initial state of charge at the start of the next charging cycle).

For example, in one or more embodiments, the data storage element 114 may maintain an array of discharge values representing the difference between the final state of charge at the end of a respective charging cycle and the initial state of charge at the start of the next following charging cycle. The weighted average of the discharge values may then be added to a reference desired minimum state of charge to arrive at an estimated state of charge required to avoid discharging the battery 106 below that minimum state of charge. In one or more embodiments, where the data storage element 114 maintains an array of 10 previous discharge amounts, the targeted final state of charge ($SOC_f$) is governed by the equation $$SOC_f = SOC_{min} + \frac{\sum_{j=0}^{9} \Delta SOC(j)}{10} + 0.5\sigma_{\Delta SOC},$$

where $SOC_{min}$ represents the desired minimum state of charge, $\Delta SOC(j)$ represents the amount of state of charge that was depleted or discharged over a preceding usage cycle, and $\sigma_{\Delta SOC}$ represents a standard deviation associated with the discharge amounts over the preceding 10 usage cycles that is utilized to add margin to the targeted final state of charge to account for potentially increased discharging over the next usage cycle and achieve a desired tradeoff between minimizing the maximum state of charge and avoiding discharge below the minimum state of charge. As the discharge amounts vary and change over time, the targeted final state of charge dynamically adapts to effectively learn the user's behavior to reduce the maximum state of charge while minimizing discharge below the minimum state of charge.

Still referring to FIG. 2, the dynamic charging process 200 also calculates or otherwise determines the estimated amount of time required to charge the energy storage element from its current initial state of charge to the targeted final state of charge (task 208). When the amount of time remaining before reaching the estimated readiness time (or expected charging cycle termination time) is greater than the estimated amount of time required to charge the energy storage element to the targeted final stage of charge, the dynamic charging process 200 charges the energy storage element at a reduced (or slower) charging rate when the current state of charge of the energy storage element is less than the holding state of charge until reaching the holding state of charge (tasks 210, 212, 214). Once the current state of charge reaches the holding state of charge, the dynamic charging process 200 maintains the energy storage element at the holding state of charge until the amount of time remaining before reaching the estimated readiness time is equal to or less than the estimated amount of time required to charge the energy storage element to the targeted final stage of charge (tasks 208, 210, 212).

In exemplary embodiments, an estimated duration of time required for an initial charging stage from the initial state of charge to the holding state of charge is determined and added to an estimated duration of time required for a final charging stage from the holding state of charge to the targeted final state of charge to arrive at an estimated total amount of time required to charge the battery 106. In exemplary embodiments, one or more of the estimated duration for the initial charging stage ($T_{CH1}$) and/or the estimated duration for the final charging stage ($T_{CH2}$) may be determined based on a reduced charging rate to be utilized during the respective charging stage, as described in greater detail below. Additionally, in some embodiments, the estimated amount of time required for a respective stage of the charging cycle is dynamically determined and updated substantially in real-time while charging to reduce the likelihood of failing to charge the battery 106 to the targeted final stage of charge, as described in greater detail below in the context of FIG. 3.

In exemplary embodiments, the estimated amounts of time required for the respective stages of the charging cycle are calculated or otherwise determined based on historical data. For example, the control system 110 and/or processing module 112 may store or otherwise maintain the respective durations of time required for the initial charging stage to the holding state of charge ($T_{CH1}$) and the final charging stage from the holding state of charge to the final state of charge ($T_{CH2}$) from previous charging cycles using reduced charging rates and average or otherwise combine the historical durations for the respective charging stages to arrive at estimated values for the respective charging stages. In one or more embodiments, a characterization procedure is performed to initially or periodically determine reference values for the estimated required charging stage durations by fully discharging the battery 106 to a state of charge of 0% then fully charging the battery 106 to a state of charge of 100% at the reduced charging rate, measuring the respective charging times, and setting charging stage durations to the measured values. For example, the measured duration of time it took to charge the battery 106 from 0% to the holding state of charge during the characterization procedure may be set as the initial value for the initial charging stage duration ($T_{CH1}$) and the measured duration of time it took to charge the battery 106 from the holding state of charge to 100% during the characterization procedure may be set as the initial value for the final charging stage duration ($T_{CH2}$). Thereafter, between iterations of the characterization procedure, the charging stage durations may dynamically update over time, as described in greater detail below.

In one or more embodiments, the estimated amount of time required for charging also incorporates an additional buffer amount of time ($T_W$) to provide a sufficient margin of time that reduces the likelihood of failing to charge the battery 106 to the targeted final stage of charge in the event of slower than expected charging of the battery 106 or a disconnection event in advance of the originally expected charging cycle termination time. In this regard, the time margin may be calculated as a percentage or function of the estimated duration for the charging cycle. For example, in one or more embodiments, the time margin or buffer is calculated as a function of the estimated duration for the charging cycle using the equation $T_W=0.05T_S+2\sigma_{T_S}$, where $\sigma_{T_S}$ represents the standard deviation associated with the duration of the preceding charging and/or discharge cycles having corresponding temporal data maintained in the data storage element 114, as described above. Thus, the buffer amount of time accounts for how much an individual user's charging or discharging behavior varies across preceding cycles and may dynamically adapt to changes in the user's behavior over time. The estimated amount of time required to charge the energy storage element to the targeted final stage of charge may be governed by the equation $T_R=T_{CH1}$ $T_{CH2}+T_W$, where $T_R$ represents the estimated amount of time required to charge the battery 106 to the targeted final state of charge that incorporates the time buffer.

Figure 3:
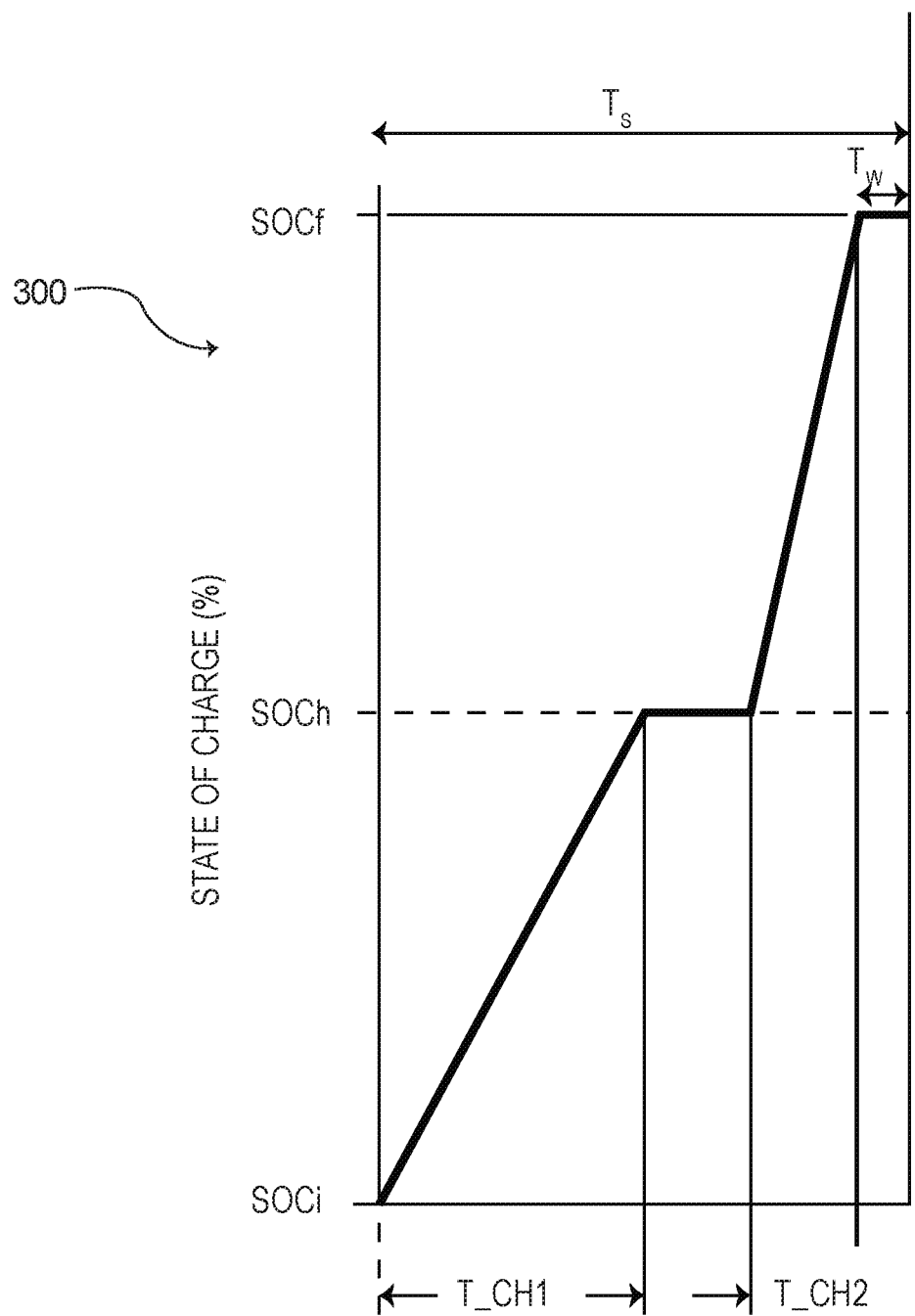
FIG. 3 is a graph depicting a state of charge of an energy storage element with respect to time in connection with an exemplary embodiment of the charging process of FIG. 2.

FIG. 3 depicts a graph 300 of a state of charge of a battery 106 with respect to time during a charging cycle for charging the battery 106 from an initial state of charge ($SOC_i$) to a targeted final state of charge ($SOC_f$) in accordance with the dynamic charging process 200 of FIG. 2. As described above, in exemplary embodiments, in response to detecting a connection event for charging the battery 106, the control module 110 and/or the processing system 112 initializes a timer or counter and calculates or otherwise determines an estimated readiness time for when the charging cycle is expected to have been completed by relative to the initialized timer or counter value (e.g., tasks 202, 204), for example, by adding the expected charging cycle duration or estimated readiness time ($T_S$) determined based on the duration of preceding charging and/or usage cycles for the battery 106 to the initial time value to arrive at a timer or counter value corresponding to the estimated readiness time. Additionally, the control module 110 and/or the processing system 112 calculates or otherwise determines the targeted final state of charge ($SOC_f$) based on historical usage data as described above (e.g., task 206). The control module 110 and/or the processing system 112 also calculates or otherwise determines the estimated duration for the initial charging stage ($T_{CH1}$) and the final charging stage ($T_{CH2}$). The illustrated graph 300 in FIG. 3 depicts a scenario where an additional margin or wait time ($T_W$) is also implemented to reduce the likelihood that the charging cycle will prematurely end before reaching the targeted final state of charge ($SOC_f$).

When the estimated amount of time remaining (e.g., the difference between the estimated readiness time and the current value of the timer or counter) is greater than the estimated amount of time required ($T_R$) to charge the battery 106 to the targeted final state of charge (e.g., $T_S-T_C \geq T_R$, where $T_R=T_{CH1}+T_{CH2}+T_W$ and $T_C$ represents the current value of the timer or counter), the control module 110 and/or the processing system 112 operates the power conversion arrangement 104 to provide current to the battery 106 to charge the battery 106 and increase the state of charge until reaching the holding state of charge ($SOC_h$). In this regard, the control module 110 and/or the processing system 112 continually monitors the output of the sensing arrangement 108 while operating the power conversion arrangement 104 to detect or otherwise identify when the current state of charge of the battery 106 is equal to the holding state of charge ($SOC_h$), for example, when the open circuit voltage of the battery 106 is equal to a voltage associated with the holding state of charge identified during the characterization procedure.

In exemplary embodiments, for the duration of the initial charging stage ($T_{CH1}$), the control module 110 and/or the processing system 112 operates the power conversion arrangement 104 to charge the battery 106 at a reduced rate, for example, by operating the power conversion arrangement 104 to enable current flow from the input interface 101 to the battery 106 at a fraction of the maximum charging current that the battery 106 is capable of receiving. In this regard, the estimated duration for the initial charging stage ($T_{CH1}$) may be calculated or otherwise determined based on the reduced rate to accommodate the reduced charging rate. In one or more embodiments, the control module 110 and/or the processing system 112 operates the power conversion arrangement 104 to provide an output charging current ($i_C$) to the battery 106 that is one-fourth of the maximum charging current capability of the battery 106 (e.g., $i_C=C/4$, where C represents the maximum charging current capability). In this regard, in practice, the reduced charging rate may be user-configurable or otherwise determined or derived from the maximum charging current in any number of different ways, and the subject matter described herein is not intended to be limited to any particular reduced charging rate. Once the current state of charge of the battery 106 reaches the holding state of charge ($SOC_h$), the control module 110 and/or the processing system 112 automatically ceases operation of the power conversion arrangement 104 in a state or configuration that prevents current flow between the input interface 101 and the battery 106 (e.g., $i_C=0$), for example, by opening or deactivating any switching elements of the power conversion arrangement 104.

In one or more embodiments, the control module 110 and/or the processing system 112 continually and dynamically determines an updated time remaining for the initial charging stage based on the current or real-time state of charge of the battery 106 during the initial charging stage. For example, the control module 110 and/or the processing system 112 may log the initial open circuit battery voltage (e.g., the voltage difference between battery terminals) and/or the initial state of charge in the data storage element 114 in association with a timestamp corresponding to the initial value of the timer or counter at the start of the charging cycle. As charging current is provided to the battery 106 during the initial charging stage, the control module 110 and/or the processing system 112 may continually log the current battery voltage (e.g., the voltage difference between battery terminals) and/or the current state of charge in the data storage element 114 in association with a timestamp corresponding to the value of the timer or counter at the time of the respective battery voltage and/or state of charge measurement. Based on the relationships between the recorded measured battery voltages and/or state of charge values and their respective times, the control module 110 and/or the processing system 112 may dynamically determine an updated estimate of the duration for the remainder of the initial charging stage ($T_{CH1}$) substantially in real-time that accounts for the battery 106 charging faster or slower than expected for the reduced charging rate. For example, during the characterization procedure, the battery voltage and corresponding state of charge may be logged and timestamped and maintained in the data storage element 114, such that the estimated remaining duration for the initial charging stage may be determined based on the difference in timestamps between a timestamped log entry that matches the current battery voltage and/or current battery state of charge and the timestamped log entry for the holding state of charge.

Still referring to FIG. 3 with continued reference to FIGS. 1-2, as time elapses during the current charging cycle, the control module 110 and/or the processing system 112 continually increments the value of the timer or counter (e.g., $T_C(n)=T_C(n)+1$) and dynamically determines an updated amount of time remaining for the charging cycle (e.g., $T_S-T_C(n)$). The state of charge of the battery 106 is maintained at the holding state of charge ($SOC_h$) as the difference between the expected charging cycle termination time ($T_S$) and the current value of the timer or counter decreases until the estimated amount of time remaining before the expected charging cycle termination time ($T_S$) is less than the estimated duration of the final charging stage ($T_{CH2}$).

Referring to FIG. 2, when the estimated amount of time remaining is less than or equal to the estimated amount of time required to finish charging the energy storage element, the dynamic charging process 200 automatically resumes charging of the energy storage element to the targeted final state of charge (task 216). In one or more exemplary embodiments, the charging rate associated with the final charging stage is dynamically determined or otherwise influenced by the amount of time remaining. For example, at the start of the final charging stage ($T_{CH2}$), the control module 110 and/or the processing system 112 may initially operate the power conversion arrangement 104 to charge the battery 106 at a reduced rate (e.g., $i_C=C/4$). In a similar manner as described above, the control module 110 and/or the processing system 112 continually logs timestamped battery voltages and/or the state of charges during the final charging stage in the data storage element 114. Based on the relationships between the recorded measured battery voltages and/or state of charge values and their respective times, the control module 110 and/or the processing system 112 may dynamically determine an updated estimate of the duration for the remainder of the final charging stage ($T_{CH2}$) substantially in real-time that accounts for the battery 106 charging faster or slower than expected for the reduced charging rate.

When the estimated amount of time required to finish charging the battery 106 to the targeted final state of charge is greater than the estimated amount of time remaining (e.g., $T_S-T_C(n)<T_{CH2}$), the control module 110 and/or the processing system 112 may dynamically increase the rate of charging by operating the power conversion arrangement 104 to charge the battery 106 at an increased rate. For example, the control module 110 and/or the processing system 112 may automatically switch to operating the power conversion arrangement 104 to charge the battery 106 at the maximum rate supported by the battery 106 (e.g., $i_C=C$) to increase the likelihood of reaching the targeted final state of charge at the estimated readiness time. It should be noted that in practice there are numerous different potential ways in which the charging rate may be dynamically varied to achieve the targeted final state of charge at the estimated readiness time, and the subject matter described herein is not intended to be limited to any particular manner of dynamically increasing the charging rate.

In exemplary embodiments, once the state of charge of the battery 106 is substantially equal to the targeted final state of charge ($SOC_f$), the control module 110 and/or the processing system 112 operates the power conversion arrangement 104 to provide a constant output voltage corresponding to the targeted final state of charge until the output current to the battery 106 is less than a termination current threshold that indicates completed charging. Once the output current to the battery 106 falls below the termination current, the control module 110 and/or the processing system 112 operates the power conversion arrangement 104 to disable current flow to the battery 106 and maintain the battery 106 at the voltage level corresponding to the targeted final state of charge (e.g., by opening all switches). Additionally, the control module 110 and/or the processing system 112 may provide a notification of charging being completed, for example, via the communications interface 120 or a user interface element associated with the charging device 102. For example, if the charging device 102 includes a display element (e.g., a light-emitting diode or the like) or a display device (e.g., a liquid crystal display or the like), the control module 110 and/or the processing system 112 may provide a graphical indication of completed charging via the display. In other embodiments, the control module 110 and/or the processing system 112 may transmit or otherwise provide a notification that charging is completed to another device via a communications network, which, in turn results in a corresponding charge completion user notification being generated at or by another device (e.g., a user's mobile phone, or the like).

Still referring to FIG. 2, in exemplary embodiments, after completing charging of the energy storage element, the dynamic charging process 200 updates the historical usage data associated with the energy storage element based on the timestamped voltage and/or state of charge values observed during the charging cycle (task 218). In this regard, the control module 110 and/or the processing system 112 may dynamically update the estimated durations of the initial charging stage ($T_{CH1}$) and the final charging stage ($T_{CH2}$) for initializing the next iteration of the dynamic charging process 200 (e.g., at task 208) to reflect the observed durations for the charging stages during the most recent charging cycle. Additionally, in response to a disconnection event (e.g., a user unplugging the input interface 101 from an external power supply or removing the battery 106 from the charging device 102), the control module 110 and/or the processing system 112 may log or otherwise record the timestamp and calculate or otherwise determine the duration of the most recent charging cycle (e.g., $T_{DISC(n)}$) based on the difference relative to the initialized timer or counter value. In this regard, when the data storage element 114 maintains an array or queue of the preceding charging cycle durations (or timestamps), the oldest entries may be evicted or otherwise overwritten with the timestamps associated with the most recent charging cycle, such that the expected charging cycle duration corresponding to the estimated readiness time ($T_S$) to be utilized during the next iteration of the dynamic charging process 200 (e.g., at task 204) is influenced by the most recent charging cycle.

Referring to FIG. 3, with continued reference to FIGS. 1-2, by virtue of the dynamic charging process 200, the duration of time (or percentage of the charging cycle) at which the battery 106 is maintained at a holding state of charge configured to minimize battery degradation may be increased, thereby prolonging lifetime. The average charging current flow to the battery 106 during the charging cycle may also be reduced to thereby help minimize the temperature of the battery 106 during charging, which also mitigates potential degradation due to charging. Additionally, the targeted final state of charge for the charging cycle may dynamically adapt and evolve to an individual user's behavior to minimize the duration of time spent at undesirably low state of charge values, while also minimizing the upper state of charge value that the battery 106 is charged to. In exemplary embodiments, the dynamic charging process 200 also reduces the duration of time that the battery 106 is at the targeted final state of charge (e.g., by maintaining the battery 106 at a more preferable holding state of charge) to reduce potential degradation due to time spent at higher state of charge values. At the same time, a buffer or wait time may be incorporated into the charging cycle that helps ensure the targeted final state of charge is achieved before use or discharge of the battery 106 is likely to be needed or desired. In this regard, it should be appreciated that there are numerous different ways in which the buffer time and reduced charging rates may be chosen or tailored to optimize the tradeoffs between the duration of time spent at the holding charge, the duration of time spent at the upper state of charge, and the amount of charging current flowing to the battery 106, and the subject matter described herein is not intended to be limited to any particular implementation.

In one or more embodiments, the dynamic charging process 200 is configured to discharge the battery 106 from the targeted final state of charge back down to the holding state of charge after maintaining the battery 106 at the targeted final state of charge for longer than a threshold duration of time. In this regard, in scenarios where the battery 106 is not returned to use within a threshold amount of time after the originally estimated charging cycle termination time, the control module 110 and/or the processing system 112 operates the power conversion arrangement 104 to discharge the battery 106 back down to a voltage level corresponding to the holding state of charge to avoid a prolonged duration at a relatively higher state of charge.

Networked Dynamic Management of Charge

Figure 4:
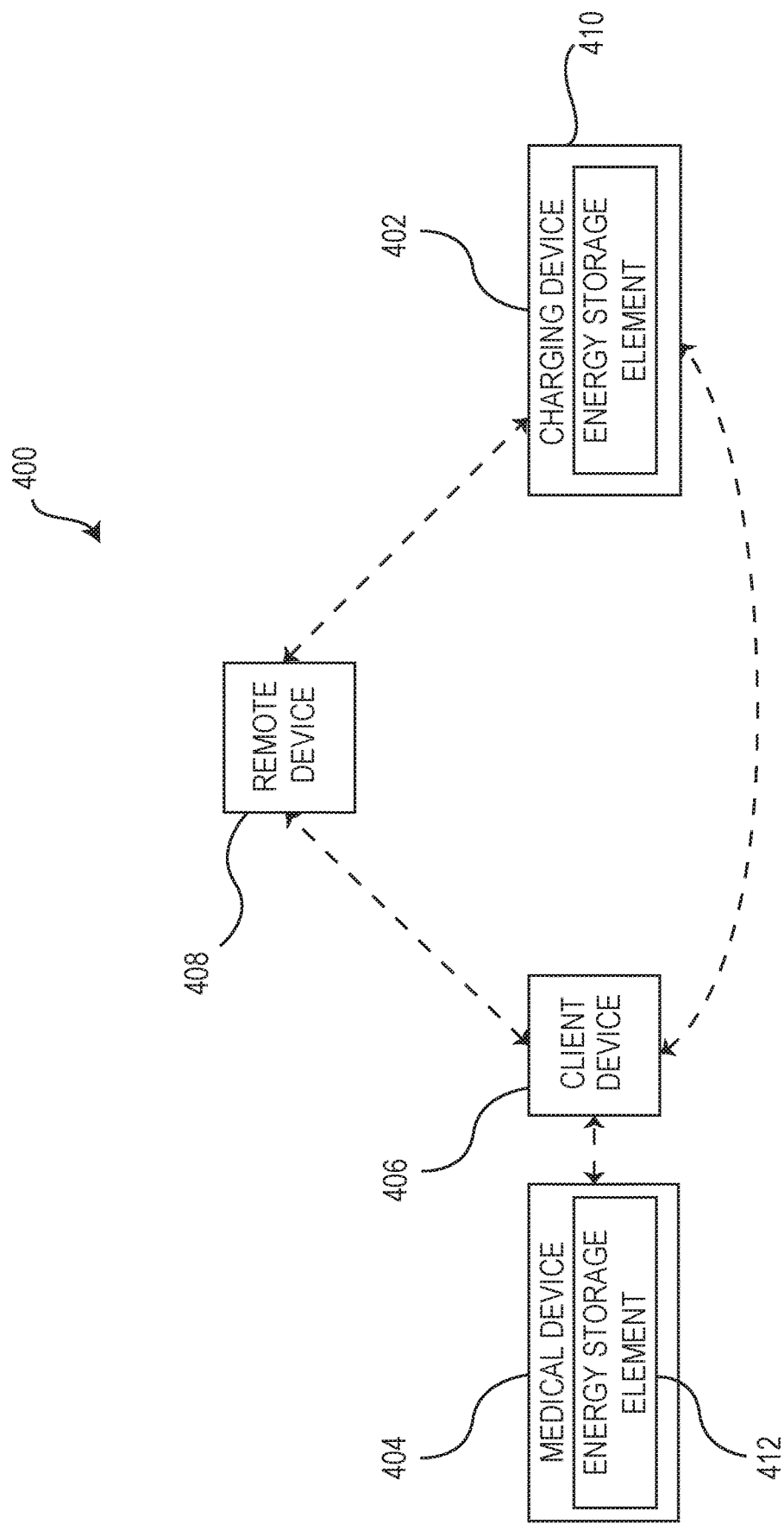
FIG. 4 is a block diagram of an exemplary patient management system suitable for implementing the charging process of FIG. 2 in one or more embodiments.
Figure 5:
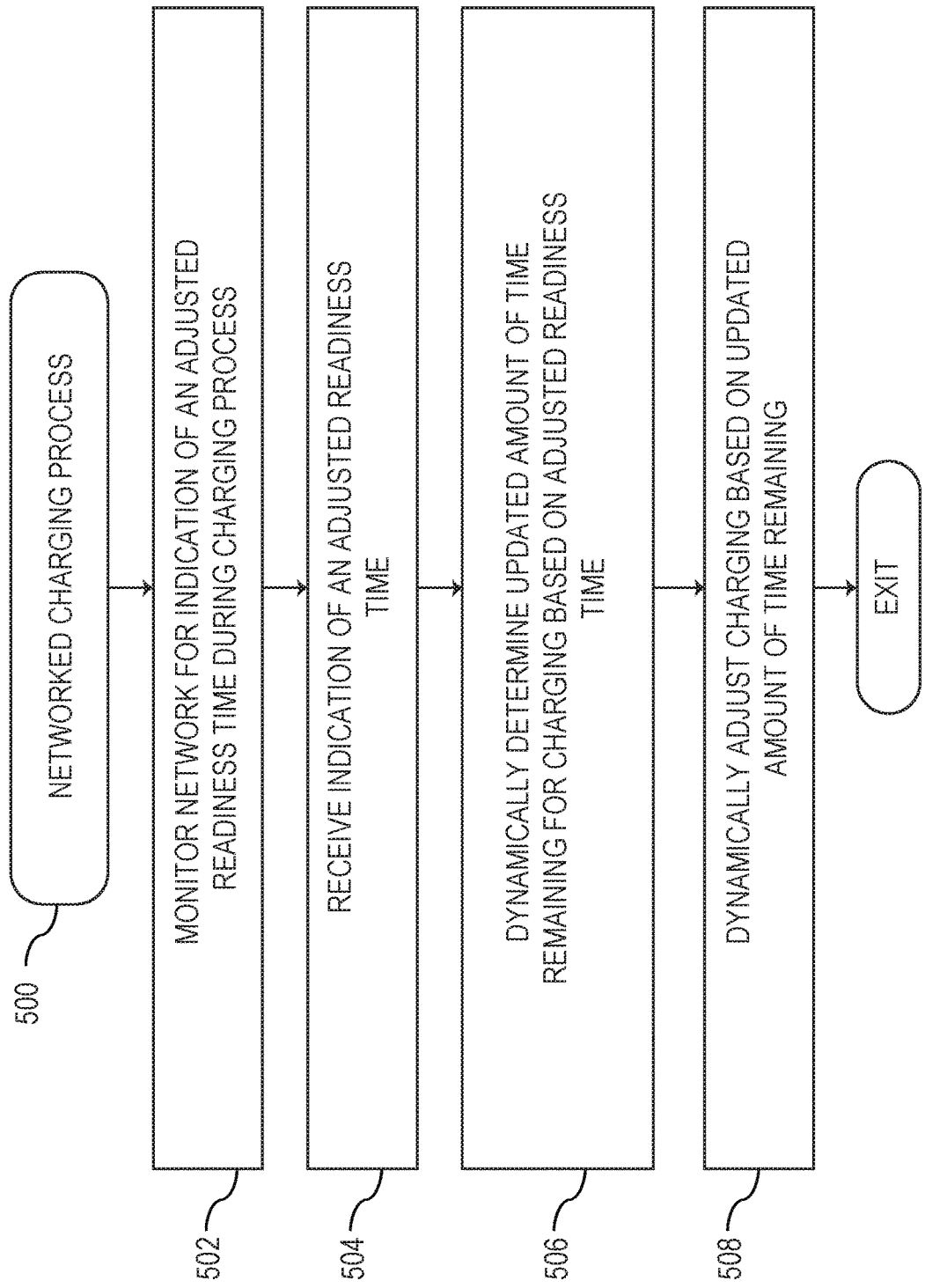
FIG. 5 is a flow diagram of an exemplary networked charging process suitable for implementation by the patient management system of FIG. 4 in one or more exemplary embodiments.

Referring now to FIGS. 4-5, and with continued reference to FIGS. 1-3, in one or more exemplary embodiments, the dynamic charging process 200 may be utilized in a networked environment to dynamically adjust the estimated charging cycle termination time, and thereby dynamically influence the charging rates to achieve the targeted final state of charge when needed or desired while otherwise maximizing the duration of time at which the battery 106 is maintained at the holding state of charge. In this regard, when the battery 106 is likely to be needed in advance of the originally estimated charging cycle termination time, a notification of an updated charging cycle termination time may be transmitted to the charging device 102 over a network. In response to receiving indication of an updated readiness time via the communications interface 120, the control module 110 and/or the processing system 112 updates or overwrites the previously estimated readiness time with an updated readiness time. An earlier readiness time decreases the estimated amount of time remaining before the expected end of the charging cycle, which in turn, may result in the charging being completed at a faster charging rate to increase the likelihood of reaching the targeted final state of charge at an earlier estimated readiness time (e.g., tasks 210, 216). Conversely, when a notification of a later readiness time is received, the estimated amount of time remaining before the expected end of the charging cycle increases, which in turn, may increase the duration of time at which the battery 106 is maintained at the holding state of charge or otherwise reduce the charging rate to prolong lifetime (e.g., tasks 210, 212, 214).

For purposes of explanation, the networked dynamic charging may be described herein in the context of one or more portable medical devices in a patient management system, such as, for example, one or more infusion devices in an insulin infusion system or one or more glucose sensing devices in a continuous glucose monitoring system. That said, it should be appreciated that the subject matter described below is not limited to medical devices or medical systems, and may be implemented in an equivalent manner in the context of other portable electronic devices or systems.

Referring to FIG. 4, in exemplary embodiments, a patient management system 400 includes, without limitation, a charging device 402, a medical device 404, a client device 406, and a remote device 408. Depending on the embodiment, two or more of the devices 402, 404, 406, 408 may be capable of communicating with one another over a communications network (or combinations thereof), such as, for example, a wireless personal area network (PAN), a wireless local area network (WLAN), a local area network (LAN), a cellular network, the Internet, and/or the like. For example, in some embodiments, the medical device 404 and/or the client device 406 may be paired with the charging device 402 to support direct communications over a wireless personal area network in a point-to-point or ad-hoc manner. In other embodiments, the medical device 404 and/or the client device 406 may communicate directly with the charging device 402 over a wireless network, a local area network, or the like, while in other embodiments the medical device 404 and/or the client device 406 may communicate indirectly with the charging device 402 via the remote device 408. For example, in one or more embodiments, the medical device 404 and client device 406 may be paired to communicate directly over a wireless point-to-point personal area network, with the client device 406 communicating with the remote device 408 over a cellular communications network or the Internet, and the remote device 408 in turn communicating with the charging device 402 over the Internet or another suitable communications network. In this regard, the subject matter described herein is not limited to any particular type, combination, or permutation of networks that may be utilized to facilitate communications and support the subject matter described herein.

The medical device 404 generally represents the component of the patient management system 400 that is configured to support management or monitoring of a patient's physiological condition. In one or more embodiments, the medical device 404 is realized as an infusion device configured to deliver a fluid, such as insulin, to the body of the patient. In such embodiments, the infusion device 404 may employ closed-loop control or other delivery control schemes that vary insulin delivery in a manner that is influenced by the patient's current glucose level received via a sensing element or other sensing device. That said, in other embodiments, the medical device 404 may be realized as a continuous glucose monitor (CGM) device or another stand-alone sensing or monitoring device, such as, for example, an interstitial glucose sensing arrangement, or similar device. Accordingly, the subject matter described herein is not limited to use with any particular type or configuration of portable medical device 404.

In exemplary embodiments, the medical device 404 generally includes a processing system, a data storage element (or memory), a communications interface, and a user interface. In this regard, the communications interface generally represents the hardware, circuitry, logic, firmware and/or other components of the medical device 404 that are coupled to the processing system for outputting data and/or information from/to the medical device 404 to/from another device 402, 406, 408 in the patient management system 400. For example, the communications interface may include or otherwise be coupled to one or more transceiver modules capable of supporting wireless communications between the medical device 404 and the client device 406, such as a Bluetooth transceiver or adapter configured to support Bluetooth Low Energy (BLE) communications.

In exemplary embodiments, the client device 406 is realized as a mobile phone, a smartphone, a tablet computer, or other similar mobile electronic device; however, in other embodiments, the client device 406 may be realized as any sort of electronic device capable of communicating with the medical device 404 and one or more other devices 402, 408 in the patient management system 400 via one or more communications networks, such as a laptop or notebook computer, a desktop computer, or the like. In some embodiments, a user, such as the patient, the patient's doctor or another healthcare provider, or the like, manipulates the client device 406 to execute a client application that supports communicating with the medical device 404 and/or other devices 402, 408 in the patient monitoring system 400. For example, the client application at the client device 406 may be configured to establish an association (or pairing) with the medical device 404 and/or the charging device 402 over a network to support subsequently establishing a point-to-point communications session between the client device 406 and a respective one of the medical device 404 and/or the charging device 402. For example, in accordance with one embodiments, the client device 406 may be paired with a respective one of the medical device 404 and/or the charging device 402 over a Bluetooth network (e.g., by obtaining and storing network identification information for the respective device 402, 404) by performing a discovery procedure or another suitable pairing procedure. The pairing information obtained during the discovery procedure allows either of the respectively paired devices to initiate the establishment of a secure communications session via a wireless personal area network.

In one or more exemplary embodiments, the client application is also configured to store or otherwise maintain a network address and/or other identification information for the remote device 408 on another communications network, which may be physically and/or logically distinct from the network(s) utilized to communicate with a respective one of the devices 402, 404, such as, for example, the Internet, a cellular network, a wide area network (WAN), or the like. In this regard, the remote device 408 generally represents a server or other computing device configured to receive and analyze or otherwise monitor measurement data, event log data, and potentially other information obtained for the patient associated with the devices 402, 404. In some embodiments, the remote device 408 may be coupled to a database configured to store or otherwise maintain data associated with individual patients. In practice, the remote device 408 may reside at a location that is physically distinct and/or separate from the other devices 402, 404, 406, such as, for example, at a facility that is owned and/or operated by or otherwise affiliated with a manufacturer of the medical device 404. For purposes of explanation, but without limitation, the remote device 408 may alternatively be referred to herein as a server.

Still referring to FIG. 4, the illustrated embodiment depicts a scenario where the charging device 402 (e.g., charging device 102) manages the charging of an energy storage element 410 that is not currently in use while another energy storage element 412 is being discharged during use by the medical device 404. In a similar manner as described above in the context of FIG. 1, the energy storage elements 410, 412 are not limited to any particular type of energy storage element; however, for purposes of explanation, but without limitation, the subject matter is described in the context of the energy storage elements 410, 412 being realized as rechargeable batteries. For example, in one or more embodiments, the charging device 402 is realized as a battery charger or the like that charges an instance of a rechargeable battery 410 that is swappable for another instance of a rechargeable battery 412 that is in use by the medical device 404. In other embodiments, the charging device 402 may be realized as a duplicative or redundant instance of the medical device 404 that is currently charging while the other instance of the medical device 404 is in use by a patient. For example, the medical device 404 may be realized as an infusion device that is currently being used by a patient to regulate his or her glycemic condition while the charging device 402 is realized as another instance of the infusion device that is being charged for later use (e.g., when the other infusion device 404 requires recharging, reservoir refilling, cannula change and/or site rotation, etc.).

Referring to FIG. 4 with reference to FIGS. 1-2, in one or more exemplary embodiments, the charging device 402 implements or otherwise performs the dynamic charging process 200 described above in the context of FIG. 2 to manage charging of the battery 410 (e.g., battery 106). For example, when the charging device 402 is plugged into an external electrical power supply or the battery 410 is removed or otherwise swapped from the medical device 404 to the charging device 402, the charging device 402 detects a connection event and initializes a timer or counter for keeping track of time while the battery 410 is being recharged (e.g., task 202). As described above, the charging device 402 may also determine the duration of the preceding usage or discharge cycle for the battery 410, that is, the duration of time during which the battery 410 was previously in use by the medical device 404 or by the charging device 402 when the charging device 402 is a duplicative or redundant instance of the medical device 404 (e.g., based on a duration of time elapsed since the preceding disconnection event with respect to the battery 410). The charging device 402 also logs the initial state of charge for the battery 410, the initial voltage of the battery 410 and/or the like for purposes of dynamically adapting the upcoming charging cycle to account for and effectively learn from the preceding usage cycle.

Based on the historical usage data associated with the battery 410, the charging device 402 calculates or otherwise determines an estimated readiness time for when the current charging cycle is expected to terminate and the battery 410 is expected to return to use (e.g., by a user swapping the recharged battery 410 for the battery 412 that was previously in use by the medical device 404) and a targeted final state of charge for the current charging cycle (e.g., tasks 204, 206). Using the initial state of charge of the battery 410 at the start of the charging cycle, the charging device 402 determines the estimated amount of time required to charge the battery 410 to the targeted final state of charge and recharges the battery 410 to the holding state of charge at a reduced charging rate when the amount of time remaining permits (e.g., tasks 208, 210, 212, 214). In this manner, the dynamic charging process 200 limits the temperature of the battery 410 during charging while also prolonging the duration of time at which the battery 410 is maintained at the holding state of charge to minimize degradation. Thereafter, as the time approaches the estimated readiness time, the charging device 402 may automatically resume charging the battery 410 to the targeted state of charge at or before the estimated time at which the battery 410 is expected to return to use (e.g., the predicted time for when a patient will swap out the discharged battery 412 currently onboard the medical device 404 for the recharged battery 410). By utilizing the dynamic charging process 200 for both batteries 410, 412, over time, the operating range for the state of charge of the batteries 410, 412 may be optimized and tailored for an individual patient's usage patterns or behaviors with respect to the medical device 404, while also minimizing degradation of the batteries 410, 412 by reducing the charging current and increasing the duration of time the batteries 410, 412 are held at an intermediate holding state of charge that minimizes degradation.

Referring now to FIG. 5, with continued reference to FIGS. 1-4, in a networked environment, communications among devices 402, 404, 406, 408 in a patient monitoring system 400 may be utilized to dynamically adjust the estimated or predicted point in time at which a charging battery 410 is expected to return to use in real-time to further improve management of the condition of the battery 410. For example, in situations where it becomes apparent that the battery 412 currently in use will remain in use longer than originally expected, the estimated readiness time may be delayed or postponed further into the future to prolong the duration of time the charging battery 410 is maintained at the holding state of charge, rather than having the charging battery 410 held at the relatively higher final state of charge for the additional duration of time during which the other battery 412 remains in use. Conversely, in situations where the charging battery 410 will likely be returned to use sooner than originally anticipated, the estimated readiness time may be advanced closer to the current time to increase the likelihood of the battery 410 achieving the targeted final state of charge before returning to use, which, in turn reduces the likelihood of the battery 410 being discharged below a minimum state of charge during the next usage cycle.

The various tasks performed in connection with the networked charging process 500 may be performed by hardware, firmware, software executed by processing circuitry, or any combination thereof. For illustrative purposes, the following description refers to elements mentioned above in connection with FIGS. 1-4. For purposes of explanation, the networked charging process 500 may be described herein primarily in the context of being implemented by a charging device 102, 402. It should be appreciated that the networked charging process 500 may include any number of additional or alternative tasks, the tasks need not be performed in the illustrated order and/or the tasks may be performed concurrently, and/or the networked charging process 500 may be incorporated into a more comprehensive procedure or process having additional functionality not described in detail herein. Moreover, one or more of the tasks shown and described in the context of FIG. 5 could be omitted from a practical embodiment of the networked charging process 500 as long as the intended overall functionality remains intact.

The networked charging process 500 initializes or otherwise begins by monitoring a communications network for an indication of an adjusted readiness time for terminating a charging process during execution of the charging process (task 502). In this regard, the control system 110 and/or processing module 112 of a charging device 102, 402 may periodically or continually monitor a communications interface 120 associated with the charging device 102, 402 for a communication that indicates a point in time for when a battery 106, 410 being charged by the charging device 102, 402 should be ready for use. It should be noted that there are any number of different conditions that may be detected by any one of the devices 404, 406, 408 in the patient monitoring system 400 and utilized to determine an estimated readiness time that triggers expediting or delaying the charging of the battery 402 in real-time, and the subject matter is not intended to be limited to any particular condition or criteria for adjusting an estimated readiness time.

For example, in one or more embodiments, the charging device 102, 402 may monitor for a wireless communication from a paired device 404, 406 over a wireless personal area network. In this regard, a medical device 404 or client device 406 paired with the charging device 402 may transmit or otherwise provide a communication that initiates establishment of a communications session for providing one or more indicia of an estimated readiness time to the charging device 402. In such embodiments, the medical device 404 or client device 406 detects or otherwise identifies a condition associated with the medical device 404 or a patient associated with the medical device 404, which, in turn triggers an indication of an estimated readiness time. For example, an application or other software module executed at the respective device 404, 406 may continually monitor the state of the in-use battery 412 (e.g., the current state of charge, the current battery voltage, and/or the like) and provide an indication to expedite or delay charging of the battery 410 based on the current status of the in-use battery 412. In this regard, when the current state of charge or voltage of the in-use battery 412 is less than a threshold (e.g., the minimum state of charge threshold), the medical device 404 may determine that charging of the battery 410 be expedited to facilitate the patient swapping the batteries 410, 412 or the devices 402, 404. In some embodiments, the medical device 404 provides a notification to the client device 406, which, in turn, initiates communications with the paired charging device 402 to provide the indication to the charging device 402. Conversely, if the in-use battery 412 is discharging at a slower than expected rate such that the current state of charge or voltage of the in-use battery 412 remains above some threshold after some period of use, the medical device 404 may determine that charging of the battery 410 can be delayed to accommodate a longer than expected usage cycle for the in-use battery 412.

As another example, when each of the charging device 402 and the medical device 404 is realized as an infusion device, the in-use infusion device 404 and/or the client device 406 may detect a low fluid condition (e.g., an amount of fluid remaining onboard the in-use infusion device that is less than a threshold), an occlusion condition, an insertion site rotation condition, or another anomalous condition for which the in-use infusion device 404 may be prematurely removed from use in favor of the redundant infusion device 402 currently being charged. As yet another example, the medical device 404 and/or the client device 406 may analyze contextual data associated with the patient to identify a contextual state or condition that triggers an indication to expedite or delay charging of the battery 410. For example, geographic location data provided by a global positioning system (GPS) receiver or similar feature of a device 404, 406 may determine whether to expedite or delay charging based on the patient's current geographic location relative to the geographic location of the charging device 402. Thus, when a patient is at work or otherwise away from home for an extended period of time while the charging device 402 located at the patient's home is charging the battery 410, the medical device 404 and/or the client device 406 may determine that charging of the battery 410 can be delayed. In such scenarios, in lieu of a wireless PAN, the medical device 404 and/or the client device 406 may provide an indication to delay charging to a remote device 408 over a communications network, such as the Internet or a cellular network. In this regard, in such embodiments, the charging device 402 may periodically poll the remote device 408 on the Internet for an indication of an estimated readiness time, or alternatively, the remote device 408 may automatically push an indication of an estimated readiness time received from one of the devices 404, 406 to the charging device 402.

Still referring to FIG. 5, the networked charging process 500 continues by receiving or otherwise obtaining an adjusted charging termination time, and in response to the adjusted readiness time, dynamically determining an updated amount of time remaining for the charging process based on the adjusted readiness time and dynamically adjusting the charging process based on the updated amount of time remaining (tasks 504, 506, 508). In this regard, when the charging device 102, 402 receives an indication of an earlier than previously anticipated readiness time, the charging device 102, 402 may expedite charging or otherwise alter the charging process to increase the likelihood of achieving the targeted final state of charge within the amount of available time remaining for charging. Conversely, when the charging device 102, 402 receives an indication of a later than previously anticipated readiness time, the charging device 102, 402 may delay charging or otherwise alter the charging process to reduce the duration of time the battery 106, 410 spends at the final state of charge, reduce the charging current flowing to (or the temperature of) the battery 106, 410, increase the duration of time spent at the holding state of charge, or take other actions to mitigate degradation of the battery 106, 410.

Referring to FIG. 5 with reference to FIGS. 1-4, in some embodiments, the networked charging process 500 is implemented in connection with the dynamic charging process 200 described above in the context of FIG. 2. In such embodiments, as the charging device 102, 402 manages the charging current and state of charge during the dynamic charging process 200, the control system 110 and/or processing module 112 monitors for potential adjustments to the readiness time via the communications interface 120. Thus, in the absence of any indication of an adjusted readiness time, the charging device 102, 402 charges the battery 106, 410 at a reduced charging rate before reaching a holding state of charge. However, in response to receiving an adjusted readiness time, the charging device 102, 402 dynamically updates the estimated amount of time remaining to charge the battery 106, 410, which, in turn, influences the manner in which the dynamic charging process 200 subsequently manages the state of charge of the battery 106, 410 (e.g., task 210).

For example, when another device 404, 406, 408 in the patient monitoring system 400 transmits an indication of an earlier estimated readiness time to the charging device 102, 402 that results in an updated estimated amount of time remaining to complete charging that is less than the time required to charge the battery 106, 410 to the targeted final state of charge given the current state of charge, the charging device 102, 402 automatically begins charging the battery 106, 410 towards the targeted final state of charge. In some embodiments, the charging device 102, 402 automatically completes charging using the maximum rate supported by the battery 106, 410 (e.g., $i_C$=C) to increase the likelihood of reaching the targeted final state of charge. However, in other embodiments, where the amount of time remaining permits, the charging device 102, 402 may operate the power conversion arrangement 104 to charge the battery 106, 410 at a reduced rate (e.g., $i_C$=C/4) in a similar manner as described above. Thus, if for some reason the medical device 404 or the client device 406 identifies a need to return the charging battery 410 to use during what would otherwise be the initial charging stage or the period of time where the charging battery 410 would have been held at the holding state of charge (e.g., the medical device 404 is low on fluid to be infused, the in-use battery 412 discharges at a faster than expected rate, etc.), the charging of the battery 410 may be expedited to allow the battery 410 to be returned to use sooner.

Conversely, in scenarios where another device 404, 406, 408 in the patient monitoring system 400 transmits an indication of a later readiness time to the charging device 102, 402 that increases the amount of time remaining to complete charging, the charging device 102, 402 may automatically reduce the rate of charging or otherwise increase the duration of time spent at the holding state of charge. For example, when the geographic location of the medical device 404 or the client device 406 or other contextual data associated with the medical device 404 or the client device 406 indicates that the patient is likely to be unable to return the charging battery 106, 410 to use for some period of time, a corresponding notification of a later readiness time may be provided to the charging device 102, 402, which, in turn, decreases the charging current and/or increases the duration of time the battery 106, 410 is maintained at the holding state of charge. Thereafter, when one of the devices 404, 406 detects a change in the contextual data that indicates the patient is likely to return the charging battery 106, 410 to use (e.g., GPS location data indicates the patient is heading home), one of the devices 404, 406 may transmit or otherwise provide a notification of an updated readiness time that reflects the change in operational context. In this regard, the updated readiness time may result in an updated estimated amount of time remaining for the charging cycle that is less than the time required to charge the battery 106, 410 to the targeted final state of charge, thereby triggering the charging device 102, 402 to automatically charge the battery 106, 410 to the targeted final state of charge at the maximum rate supported by the battery 106, 410. Thus, in addition to the dynamic charging process 200 adapting to a patient's historical behavior, the networked charging process 500 may be utilized to further adapt the current charging cycle to the patient's current behavior substantially in real-time. In some embodiments, when an indication of a later readiness time is received during the final charging stage or after the battery 106, 410 has reached the targeted final state of charge, the charging device 102, 402 may automatically discharge the battery 106, 410 back down to the holding state of charge when the updated amount of time remaining is greater than a threshold, thereby mitigating potential degradation or aging attributable to time spent at the upper state of charge.

It should be noted that in some embodiments, the indication of an adjustment to the estimated readiness time may also include or otherwise be accompanied by an indication of an adjusted final state of charge for the current charging cycle of the battery 106, 410. For example, in addition to providing an indication of an earlier readiness time when the in-use battery 412 becomes depleted or discharged faster than anticipated, the medical device 404 or the client device 406 may provide an increased targeted final state of charge to the charging battery 410 to proactively compensate for a potentially increased rate of discharge. Accordingly, when implemented in conjunction with the dynamic charging process 200 of FIG. 2, in addition to dynamically determining an updated amount of available time remaining, the charging device 102, 402 also dynamically determines an updated amount of time required to charge the battery 106, 410 that reflects the adjusted final state of charge target (e.g., task 208). Thus, either the adjustment to the readiness time or the final state of charge target may influence the manner in which charging of the battery 106, 410 is completed. In an equivalent manner, the medical device 404 or the client device 406 may provide a reduced targeted final state of charge, which may delay the final charging stage, reduce the final charging stage charging current, and/or prolong the duration of time spent at the holding state of charge. In this regard, it should be noted that in some embodiments, the networked charging process 500 may be implemented in an equivalent manner and achieve equivalent functionality by adjusting the targeted final state of charge for the battery 106, 410 without adjusting the estimated readiness time.

In other embodiments, the charging device 102, 402 may be configured to automatically determine an updated final state of charge target based on the adjustment to the readiness time. For example, in response to an indication to advance the readiness time and reduce the duration of the charging cycle by five percent, the control system 110 and/or the processing module 112 may automatically increase the targeted final state of charge by five percent to account for a potentially increased rate of discharge during the upcoming usage cycle or a potentially prolonged duration of usage of the battery 106, 410 during the upcoming usage cycle.

By virtue of the networked charging process 500, charging of a battery 410 not currently in use may be managed in a manner that mitigates degradation of the battery 410 while also facilitating the availability of the battery 410 to return to use as needed in response to unpredictable changes or variations. This is advantageous for medical applications that require substantially uninterrupted usage of a medical device 404, such as, for example, closed-loop glycemic control, continuous glucose monitoring, and the like. For example, when the medical device 404 is realized as a portable insulin infusion device that provides closed-loop control of a patient's glucose level, improved glycemic control may be achieved by having another charged battery 410 ready for deployment when the battery 412 in use becomes prematurely discharged or otherwise depleted. Thus, when the in-use battery 412 falls below a threshold state of charge, the charging device 402 may be notified via a network to complete charging of the battery 410, so that the batteries 410, 412 may be swapped with limited interruption to the closed-loop glycemic control provided by the infusion device 404. Likewise, when the charging device 402 is realized as a redundant instance of a medical device 404 that requires premature or unanticipated recharging, replacement, maintenance, or other modifications, the charging device 402 may be notified to complete charging so that the patient may swap devices 402, 404 with limited interruption or inconvenience. Additionally, by integrating the networked charging process 500 with the dynamic charging process 200 that adapts to the patient's historical behavior, the lifetime and performance of the batteries 410, 412 may be prolonged, thereby reducing battery replacement costs and further improving the patient experience.

For the sake of brevity, conventional techniques related to batteries and energy storage, power conversion and charging, portable electronic devices, infusion systems, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. Thus, although various drawing figures may depict direct electrical connections between components, alternative embodiments may employ intervening circuit elements and/or components while functioning in a substantially similar manner.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A processor-implemented method comprising:
obtaining a first estimated readiness time for an energy storage element that is interchangeable with an in-use energy storage element;
obtaining a target state of charge for the energy storage element;
calculating an estimated charging time based at least in part on a difference between the target state of charge and a current state of charge of the energy storage element and at least one of a first charging rate or a second charging rate;
responsive to determining that an amount of time remaining before reaching the first estimated readiness time is greater than the estimated charging time, using the first charging rate to charge the energy storage element to an intermediate state of charge;
maintaining the energy storage element at the intermediate state of charge;
while maintaining the energy storage element at the intermediate state of charge, determining an updated estimated charging time based on (1) a difference between the target state of charge and the intermediate state of charge and (2) the first charging rate;
obtaining an indication of a second estimated readiness time that is triggered upon identification of an anomalous condition of a device powered by the in-use energy storage element, the anomalous condition resulting in the in-use energy storage element being prematurely removed from use, the second estimated readiness time being earlier than the first estimated readiness time;
while maintaining the energy storage element at the intermediate state of charge, determining that an amount of time remaining before reaching the second estimated readiness time is less than the updated estimated charging time; and
responsive to determining that the amount of time remaining before reaching the second estimated readiness time is less than the updated estimated charging time, using the second charging rate to charge the energy storage element to the target state of charge, wherein the second charging rate is greater than the first charging rate.

2. The method of claim 1, wherein obtaining the first estimated readiness time comprises determining the first estimated readiness time based on historical usage data associated with the energy storage element.

3. The method of claim 2, wherein the historical usage data comprises timestamped data associated with preceding charging cycles, and wherein determining the first estimated readiness time comprises:
   determining respective durations of the preceding charging cycles based at least in part on the timestamped data; and
   determining the first estimated readiness time relative to an initial time for a current charging cycle based at least in part on an average of the respective durations of the preceding charging cycles.

4. The method of claim 1, wherein obtaining the target state of charge comprises determining the target state of charge based on historical usage data associated with the energy storage element.

5. The method of claim 4, wherein determining the target state of charge comprises adding an average amount of discharge associated with the energy storage element over one or more preceding usage cycles to a desired minimum state of charge threshold.

6. The method of claim 5, further comprising determining a respective discharge for each usage cycle of the one or more preceding usage cycles based at least in part on a difference between a final state of charge associated with a preceding charging cycle and an initial state of charge of the energy storage element for a current charging cycle.

7. The method of claim 1, wherein calculating the estimated charging time comprises:
   determining a first estimated duration for an initial charging stage based on a difference between the current state of charge and the intermediate state of charge and the first charging rate;
   determining a second estimated duration for a final charging stage based on a difference between the target state of charge and the intermediate state of charge and the second charging rate; and
   determining the estimated charging time based on a sum of the first estimated duration and the second estimated duration.

8. The method of claim 7, wherein determining the estimated charging time comprises adding a buffer amount of time to the sum of the first estimated duration and the second estimated duration.

9. The method of claim 8, further comprising determining the buffer amount of time based at least in part on a standard deviation associated with durations of preceding charging cycles, wherein the estimated readiness time is determined relative to an initial time for a current charging cycle based at least in part on an average of the durations of the preceding charging cycles.

10. The method of claim 1, wherein obtaining the indication of the second estimated readiness time comprises receiving the indication of the second estimated readiness time via a network.

11. The method of claim 1, wherein obtaining the target state of charge comprises receiving an indication of the target state of charge via a network.

12. One or more non-transitory processor-readable storage media storing instructions that, when executed by one or more processors, cause performance of:
   obtaining a first estimated readiness time for an energy storage element that is interchangeable with an in-use energy storage element;
   obtaining a target state of charge for the energy storage element;
   calculating an estimated charging time based at least in part on a difference between the target state of charge and a current state of charge of the energy storage element and at least one of a first charging state or a second charging state;
   responsive to determining that an amount of time remaining before reaching the first estimated readiness time is greater than the estimated charging time, using the first charging rate to charge the energy storage element to an intermediate state of charge;
   maintaining the energy storage element at the intermediate state of charge;
   while maintaining the energy storage element at the intermediate state of charge, determining an updated estimated charging time based on (1) a difference between the target state of charge and the intermediate state of charge and (2) the first charging rate;
   obtaining an indication of a second estimated readiness time that is triggered upon identification of an anomalous condition of a device powered by the in-use energy storage element, the anomalous condition resulting in the in-use energy storage element being prematurely removed from use, the second estimated readiness time being earlier than the first estimated readiness time;
   while maintaining the energy storage element at the intermediate state of charge, determining that an amount of time remaining before reaching the second estimated readiness time is less than the updated estimated charging time; and
   responsive to determining that the amount of time remaining before reaching the second estimated readiness time is less than the updated estimated charging time, using the second charging rate to charge the energy storage element to the target state of charge, wherein the second charging rate is greater than the first charging rate.

13. The one or more non-transitory processor-readable storage media of claim 12, wherein the target state of charge is determined by adding average discharges of the energy storage element over one or more preceding usage cycles to a minimum threshold state of charge.

14. The one or more non-transitory processor-readable storage media of claim 12, wherein calculating the estimated charging time comprises:
   determining a first estimated duration for an initial charging stage based on a difference between the current state of charge and the intermediate state of charge and the first charging rate;
   determining a second estimated duration for a final charging stage based on a difference between the target state of charge and the intermediate state of charge and the second charging rate; and
   determining the estimated charging time based on a sum of the first estimated duration and the second estimated duration.

15. The one or more non-transitory processor-readable storage media of claim 12, wherein obtaining the first estimated readiness time comprises determining the first estimated readiness time based on historical usage data associated with the energy storage element.

16. The one or more non-transitory processor-readable storage media of claim 12, wherein obtaining the target state of charge comprises determining the target state of charge based on historical usage data associated with the energy storage element.

17. A system comprising:
one or more processors; and
one or more processor-readable storage media storing instructions which, when executed by the one or more processors, cause performance of:
obtaining a first estimated readiness time for an energy storage element that is interchangeable with an in-use energy storage element;
obtaining a target state of charge for the energy storage element;
calculating an estimated charging time based at least in part on a difference between the target state of charge and a current state of charge of the energy storage element and at least one of a first charging rate or a second charging rate;
responsive to determining that a time difference between an amount of time remaining before reaching the first estimated readiness time and a first point in time is greater than the estimated charging time, using the first charging rate to charge the energy storage element to an intermediate state of charge;
maintaining the energy storage element at the intermediate state of charge;
while maintaining the energy storage element at the intermediate state of charge, determining an updated estimated charging time based on (1) a difference between the target state of charge and the intermediate state of charge and (2) the first charging rate;
obtaining an indication of a second estimated readiness time that is triggered upon identification of an anomalous condition of a device powered by the in-use energy storage element, the anomalous condition resulting in the in-use energy storage element being prematurely removed from use, the second estimated readiness time being earlier than the first estimated readiness time;
while maintaining the energy storage element at the intermediate state of charge, determining that an amount of time remaining before reaching the second estimated readiness time is less than the updated estimated charging time; and
responsive to determining that a time difference between the estimated readiness time and a second point in time is less than the amount of time remaining before reaching the second estimated readiness time is less than the updated estimated charging time, using the second charging rate to charge the energy storage element to the target state of charge, wherein the second point in time is after the first point in time, and wherein the second charging rate is greater than the first charging rate.

18. The system of claim 17, further comprising a portable medical device, wherein the portable medical device comprises the one or more processors.

19. The system of claim 17, further comprising a battery charger, wherein the battery charger comprises the one or more processors.

20. The system of claim 17, wherein the second charging rate corresponds to a maximum charging current capability associated with the energy storage element.

\* \* \* \* \*